United States Patent [19]

Ohkoshi et al.

[11] Patent Number: 5,705,682
[45] Date of Patent: Jan. 6, 1998

[54] PROCESS FOR PRODUCING HIGHLY PURE TEREPHTHALIC ACID

[75] Inventors: Fumio Ohkoshi; Masato Inary; Fumiya Zaima, all of Kurashiki, Japan

[73] Assignees: Mitsubishi Gas Chemical Company, Inc., Tokyo; Toyo Boseki Kabushiki Kaisha, Osaka; Mizushima Aroma Company, Ltd., Kurashiki, all of Japan

[21] Appl. No.: 706,890

[22] Filed: Sep. 3, 1996

[30] Foreign Application Priority Data

Sep. 22, 1995 [JP] Japan ................................. 7-244196

[51] Int. Cl.⁶ ........................................... C07C 51/16
[52] U.S. Cl. ................................... 562/414; 562/413
[58] Field of Search ........................... 562/413, 414

[56] References Cited

U.S. PATENT DOCUMENTS 4,939,297  7/1990  Browder et al. .

FOREIGN PATENT DOCUMENTS 1 152 576  5/1969  United Kingdom .
2 067 563  7/1981  United Kingdom .

*Primary Examiner*—Samuel Barts
*Attorney, Agent, or Firm*—Frishauf, Holtz, Goodman, Langer & Chick, P.C.

[57] ABSTRACT

A process for producing highly pure terephthalic acid comprising: (a) oxidizing a p-phenylene compound in the liquid phase in the presence of acetic acid, to produce a liquid-phase oxidation product, (b) separating the liquid-phase oxidation product into the following: (i) a first mother liquid containing acetic acid and (ii) a crude terephthalic acid, (c) evaporating, in whole or in part, the first mother liquid, to produce a vapor, (d) feeding the vapor, or a condensate thereof, to an intermediate stage of a distillation tower, carrying out an azeotropic distillation and withdrawing through a bottom of the distillation tower a concentrated acetic acid, (e) subjecting the crude terephthalic acid to a refining treatment, which is a catalytic hydrotreatment, a catalytic treatment or a recrystallization, which is carried out in the presence of is water, (f) cooling and crystallizing the resultant liquid from step (e), to produce a pure terephthalic acid and a second mother liquor, (g) subjecting the second mother liquor to an extraction in the presence of an azeotrope-forming agent to extract aromatic carboxylic acids contained in second mother liquor, to produce a liquid extract, and (h) recycling the liquid extract to the distillation tower in step (d). The process can greatly reduce the effluent water treatment load and enhance the yield of the objective terephthalic acid, in addition to providing recycling of useful reactants.

14 Claims, No Drawings

PROCESS FOR PRODUCING HIGHLY PURE TEREPHTHALIC ACID

BACKGROUND OF THE INVENTION

1. Field of the Invention

The present invention relates to a process for producing highly pure terephthalic acid which is the principal starting raw material for a polyester resin employed in fibers, films, industrial members, general molded articles and the like. More particularly, it pertains to a process for treating the mother liquor which is generated in the case of the production of the highly pure terephthalic acid.

2. Description of Related Arts

In general, terephthalic acid is produced by oxidizing p-xylene with molecular oxygen, that is, mainly air at a high temperature and a high pressure by the use of acetic acid as a solvent in the presence of a catalyst such as cobalt and manganese along with a promoter such as a bromine compound or in the presence of a cobalt catalyst together with an accelerator such as acetaldehyde.

However, the terephthalic acid produced by such liquid-phase oxidation is usually poor in whiteness and contains a considerable amount of impurities such as 4-carboxybenzaldehyde (4CBA) and p-toluic acid, thereby making it unsuitable to employ itself as such for the production of a polyester by reacting with a glycol.

As processes for producing highly pure terephthalic acid by purifying crude terephthalic acid containing impurities such as 4CBA, mention is made of various known processes for the refining treatment such as oxidation, reduction and recrystallization alone. Of these, there is commercially available a purifying process by catalytically hydrotreating the aqueous solution of crude terephthalic acid, exemplified by a purifying process by catalytically hydrotreating the aqueous solution of crude terephthalic acid at an elevated temperature. There are also proposed many processes improved over the above-mentioned process.

According to the aforesaid process, however, the mother liquor remaining after the separation of the crystals of the highly pure terephthalic acid (hereinafter referred to as "PTA mother liquor") contains aromatic carboxylic acids such as p-toluic acid, benzoic acid and the like in addition to the terephthalic acid the quantity of which corresponds to the solubility thereof. Thus, in the case of discarding this PTA mother liquor, it is obliged to treat the aromatic carboxylic acids each having a high biochemical oxygen demand (BOD), and besides such treatment leads to the loss of materials with economical value such as terephthalic acid, p-toluic acid which can be converted into terephthalic acid, and the like. It is also required to use a large quantity of water several times as large as the quantity of the produced highly pure terephthalic acid and to discharge the water after the treatment.

The concentrations of the aromatic carboxylic acids that are contained in the PTA mother liquor vary depending upon the quality of the crude terephthalic acid, reaction conditions in the catalytic hydrotreatment, crystallization conditions and separation conditions. The PTA mother liquor, which usually contains 100 to 1000 ppm of terephthalic acid, 300 to 3000 ppm of p-toluic acid and 50 to 500 ppm of benzoic acid, is transferred to an effluent water treatment unit to be subjected to activated sludge treatment or the like therein, and thereafter is discharged from the unit.

Since a commercial production plant for terephthalic acid is a huge plant, it is necessary to treat a large amount of PTA mother liquor as effluent water, which sometimes amounts to 50 to 150 $m^3$/hour per one effluent treatment unit, thus requiring great expenses for the investment of the treatment unit and the operation of the unit including manpower.

Furthermore, the loss due to the discharge of the useful substances such as terephthalic acid and p-toluic acid that are contained in the PTA mother liquor, in addition to the above-mentioned expenses for the effluent treatment unit and the operation thereof, results in an increase in the production cost of highly pure terephthalic acid.

SUMMARY OF THE INVENTION

It is a general object of the present invention to provide a process for producing highly pure terephthalic acid which process is capable of recovering useful components contained in the PTA mother liquor and greatly reducing the effluent water treatment load without requiring particular investment and operation expenses, thereby curtailing the economical loss concerned with the treatment of the PTA mother liquor which is separated during the course of producing highly pure terephthalic acid.

Other objects of the present inveiton will in part be obvious and will in part appear hereinafter.

Under such circumstances, intensive research and investigation were made by the present inventors on the process for producing highly pure terephthalic acid involving the above-mentioned problems. As a result, it has been found that the aforesaid objects of the present invention are achieved by a process which comprises the steps of extracting the useful components contained in the PTA mother liquor remaining after the separation of the highly pure terephthalic acid by means of an azeotrope-forming agent to be employed in a distillation tower for discharging, outside the reaction system, the water formed from the mother liquor from oxidation reaction that is obtained through the liquid-phase oxidation reaction; and treating the resultant extract in the form of liquid which contains the aforesaid azeotrope-forming agent by the use of the distillation tower. That is to say, the aforestated process enables the effluent water treatment load to be greatly reduced, and at the same time, the raffinate, that is, the water separated from the extract to be recycled as a solvent. The present invention has been accomplished on the basis of the above-mentioned finding and information. That is to say, the present invention is concerned with a process for producing highly pure terephthalic acid by subjecting a p-phenylene compound to liquid-phase oxidation in the presence of acetic acid as a solvent, producing highly pure terephthalic acid through the refining treatment of the crude terephthalic acid separated from the resultant reaction liquid, separating water through the azeotropic distillation of the mother liquor from the oxidation reaction separated from the crude terephthalic acid, and recycling the resultant water-free mother liquor as the solvent for the liquid-phase oxidation which process comprises the steps of a) separating the liquid-phase oxidation product into the mother liquor from the oxidation reaction and the crude terephthalic acid, and then evaporating in part or in whole, the mother liquor from the oxidation reaction containing acetic acid as a solvent; b) subjecting the resultant crude terephthalic acid to refining treatment by means of catalytic hydrotreatment, catalytic treatment or recrystallization by the use of water as a solvent and thereafter separating said acid into the mother liquor and terephthalic acid crystals through the cooling and crystallization of the liquid thus subjected to refining treatment; c) subjecting the mother liquor produced in the preceding step b) to extracting treatment by the use of an azeotrope-forming agent to extract aromatic carboxylic acids contained in said mother liquor into the agent; and d) feeding the vapor generated by the evaporation of the mother liquor from the oxidation reaction in the step a) or condensate thereof to an intermediate stage of a distillation tower and feeding the liquid extract obtained in the step c) to the distillation tower to proceed with azeotropic distillation, withdrawing, through the bottom thereof, the concentrated acetic acid thus separated from the water by the azeotropic distillation, and distilling away, through the top thereof, an azeotropic mixture of water and the azeotrope forming agent.

DESCRIPTION OF PREFERRED EMBODIMENT

In the step a), at first a p-phenylene compound is subjected to liquid-phase oxidation for the production of crude terephthalic acid. The p-phenylene compound to be employed shall be a phenylene compound having carboxyl groups at para positions or substituent groups subject to oxidation which form carboxyl groups by liquid-phase air oxidation at said positions. Examples of the substituent group include a methyl group, an ethyl group, a propyl group, an isopropyl group, a formyl group and an acetyl group. The substituent group may be the same as or different from each other. The most prevailing p-phenylene compound to be used is p-xylene.

There is used acetic acid or acetic acid containing water as a solvent in the liquid-phase oxidation. There are used a compound of a transition metal such as manganese, cobalt, iron, chromium or nickel as a catalyst and, as the case may be, a bromine compound as a promoter or co-catalyst. The catalyst and promoter are not specifically liminted provided that manganese, cobalt, iron, chromium, nickel or bromine forms manganese ions, cobalt ions, iron ions, chromium ions, nickel ions or bromine ions, respectively.

In the case where a bromine compound as a co-catalyst is not used, there may be used acetaldehyde or methyl ethyl ketone as an accelerator in combination with a cobalt catalyst. Examples of usable oxidizing agents include molecular oxygen, air in general, air which is increased in oxygen concentration by mixing gaseous oxygen therein, and conversely air which is decreased in oxygen concentration by mixing an inert gas such as gaseous nitrogen therein.

The adoptable reaction temperature at the time of liquid-phase oxidation is in the range of from 160° C. to 220° C. The reaction pressure needs only be in the range enabling the acetic acid containing water as a solvent to be maintained in a liquid phase. In the case where a bromine compound as a co-catalyst is not used, an oxidation reaction temperature of not higher than 160° C. is adopted in many cases.

The liquid-phase oxidation is put into practice by means of one or more reactors. The reaction liquid after the completion of the oxidation reaction is transferred to one or more continuously arranged crystallizers whose internal pressures are consecutively decreased, and is cooled therein to the temperature corresponding to the respective pressures by the flash cooling function of the solvent to form terephthalic acid, most of which is crystallized so as to produce a slurry solution. The resultant slurry solution is separated into crude terephthalic acid in the form the of cake and mother liquor from oxidation reaction by a crystal separating means, for example, a rotary vacuum filter means, a centrifugal separation means or an other suitable separation means.

A part of the mother liquor from the oxidation reaction is recycled as the solvent to be reused in the step a), usually as it is, or through an oxidation treatment, a reduction treatment or the like. The balance thereof is separated mainly into acetic acid, vapor composed of steam and a low boiling point product, and residue on evaporation for the purpose of removing water and byproducts that are formed in the oxidation reaction by vaporizing in an ordinary evaporator or a film evaporator. The aforesaid steam is sent to an intermediate stage of a distillation tower in the step d), while the residue on evaporation is subjected to various treatment steps to recover the catalyst as a useful component, and unnecessary products are discarded.

The crude terephthalic acid in the form of a cake is washed as necessary with acetic acid or water and is sent to a dryer, where the adherent solvent is removed to form crude terephthalic acid.

The above-mentioned step a) has for many years actually been used as a process for producing crude terephthalic acid on a commercial scale. For example, Japanese Patent Application Laid-Open No. 160942/1989 (EP-A-321272) discloses a process in which a slurry solution formed in consecutively depressurized crystallizers is fed to a mother liquor replacement tower, where the mother liquor from the oxidation reaction is replaced with water which is fed from the bottom portion of the tower, and the resulting slurry of the crude terephthalic acid in water as the solvent is transmitted as it is to a catalytic hydrotreatment step. The acetic-acid-containing solution which is separated in the mother liquor replacement tower may be sent to a distillation tower in the step d) of the present invention.

A refining step is necessary for the crude terephthalic acid obtained from the liquid-phase oxidation, since the acid contains a variety of impurities typified by 4 CBA and the value of its $OD_{340}$, which is an index of the hue, is not in the level enabling it to be directly used as a raw material of a polymer for various uses.

A process for producing highly pure terephthalic acid by purifying crude terephthalic acid is exemplified by many processes such as a catalytic hydrotreatment, a catalytic treatment, oxidation treatment and recrystallization alone, any of which is usable in the process according to the present invention. In the following, some description will be given of the catalytic hydrotreatment which is most prevailing among them.

There is used, as the catalyst in the catalytic hydrogenation reaction, a noble metal belonging to the group 8 of the Periodic table, which is preferably exemplified by palladium, platinum, ruthenium and rhodium, particularly preferably by palladium. The above-mentioned metal may be used alone or in combination with at least one other, and is usually supported on a carrier. Usually a porous material is used as a carrier, which is preferably a carbonaceous carrier from the viewpoint of material. The suitable carrier is activated carbon, especially granular activated carbon made from crushed coconut shell. The amount of the above-mentioned metal to be supported on the carrier is not specifically limited as even a slight amount thereof is effective, but it is preferably in the range of from 0.1 to 1.0% by weight in order that the catalytic activity may be maintained for a long period of time.

The catalytic hydrotreatment is carried out in a state of an aqueous solution under a high pressure at an elevated temperature of not lower than 250° C., preferably in the range of from 260° C. to 300° C. in the presence of hydrogen.

The hydrotreatment pressure needs only to be sufficient for maintaining a liquid phase and besides be capable of keeping an appropriate hydrogen partial pressure, and it is usually 50 to 100 atm.

The catalytic hydrotreatment time needs only to be sufficient for substantially proceeding with the hydrogenation reaction, and it is usually 1 to 60, preferably 2 to 20 minutes.

The catalytic hydrotreatment is put into practice usually in a continuous system. The aqueous solution of terephthalic acid formed by the catalytic hydrotreatment is usually filtered to prevent the fine powders of a worn catalyst such as activated carbon from mixing in the product. Then, the resultant filtrate is transmitted to 2 to 6 stages of crystallizers that are connected in series or a batch crystallizer, consecutively depressurized to evaporate water and cool itself, and made into a slurry solution by the deposition of terephthalic acid crystals.

The resultant slurry solution is separated into terephthalic acid in the form of a cake and a PTA mother liquor by a crystal separating means such as a rotary vacuum filter means or a centrifugal separation means.

The temperature at the time of separating the slurry solution is not specifically restricted, but is usually selected in the range of from 70° to 160° C. In the case of separation at a high temperature, the cake thus obtained is made into a slurry with water and again separated in most cases.

In the case where the above-mentioned mother liquor replacement method is employed, there is adopted a method in which the slurry solution is introduced in a mother liquor replacement tower in a state of a relatively high temperature of about 120° to 200° C., the mother liquor is replaced with water, and the resulting slurry solution is further decreased in temperature to form terephthalic acid which is separated.

The terephthalic acid cake thus obtained is subjected to a drying step to produce highly pure terephthalic acid as the finished product.

The step c) is a step of extracting aromatic carboxylic acids, that is, principally p-toluic acid and benzoic acid that are contained in PTA mother liquor by bringing the PTA mother liquor into contact with an azeotrope forming agent.

The aforesaid azeotrope forming agent is used for the purpose of azeotropic distillation for the mother liquor from the oxidation reaction produced after the separation of the crude terephthalic acid. In general, well-known compounds that are used in the azeotropic distillation for a mixed solution of acetic acid and water, are applicable to the present case. Examples thereof include toluene, xylene, ethylbenzene, methyl butyl ketone, chlorobenzene, ethyl amyl ether, butyl formate, n-butyl acetate, isobutyl acetate, amyl acetate, n-butyl propionate and isobutyl propionate. Of these, n-butyl acetate is most preferable.

As a specific embodiment in the present invention, mention is made of the step in which the extraction is carried out by the use of a mixture of the azeotrope forming agent and water which mixture is azeotropically distilled in the distillation tower and discharged at the top thereof. Alternatively, the aforesaid mixture is separated in a decanter or the like so that the separated azeotrope forming agent is used for the extraction. Although there is not much difference in the extraction efficiency between the two embodiments, the former embodiment is advantageous in that it can simplify the step. The azeotrope forming agent which has been used in the extraction is again employed as the azeotrope forming agent in the distillation toweer.

The extraction temperature is not specifically limited, but when set to a temperature which is not widely apart from the azeotropic temperature of the mixture of the azeotrope forming agent and water under atmospheric pressure, it is useful in saving thermal energy with respect to a specific embodiment. Preferably it is set to a temperature lower than the azeotropic temperature by at most 20° C.

The amount of the azeotrope forming agent to be used is not specifically limited, but is preferably in the range of 0.1 to 2 parts by weight based on 1 part by weight of the PTA mother liquor. In the aforesaid method, however, it is frequently restricted by the flow rate of the azeotrope forming agent which is distilled away from the distillation tower.

There is employed a well-known extraction apparatus, usually a countercurrent multi-stage extraction apparatus. As is clear from the examples, a sufficiently great partition ratio, that is, the ratio of the concentration of aromatic carboxylic acids in the layer of the azeotrope forming agent to the concentration of the same in the water layer, can exhibit a satisfactory effect even with a single-stage extraction method in which an extracting vessel is combined with a decanter. A multi-stage extraction method is also satisfactory in which an extraction vessel is combined in series with a decanter.

The step d) comprises recovering, in a distillation tower, acetic acid to be used as a solvent for the liquid-phase oxidation reaction. The steam or condensate thereof which is sent from the step a) contains water formed from the result of oxidation reaction in addition to acetic acid and low boiling point byproducts. The water is separated in the distillation tower so that it is discharged outside the reaction system. In this step d), the steam or condensate thereof which is sent from the ordinary evaporator or the film evaporator in the step a) is fed in an intermediate stage of the distillation tower, in the bottom of which is formed acetic acid dehydrated to the extent that the acid is usable in the liquid-phase oxidation reaction. In this case, the azeotrope forming agent is fed to the tower at the top portion or an other portion. The distillate discharged at the top of the tower is substantially the azeotropic mixture of water and the azeotrope forming agent, so that it contains only a slight concentration of acetic acid.

The azeotropic mixture which is distilled away through the top of the tower is separated into the azeotrope forming agent and water by means of a proper separating unit such as a decanter. The water is discharged in part outside the reaction system, but refluxed in part to the top portion of the tower. The reflux ratio in this step is set usually in the range of from 0.1 to 3, approximately. Here, the reflux ratio is defined by the following formula.

$$\text{Reflux ratio} = \frac{a}{b-a}$$

where a: reflux water rate (m$^3$/hr)

b: flow rate of water distilled away through the top of tower (m$^3$/hr).

The azeotrope forming agent which is separated in the decanter or the like is used as the extraction agent in the step c), again fed to the distillation tower.

As can be seen from the working examples hereinafter described, the above-mentioned process makes it possible to keep a low concentration of the aromatic carboxylic acids in the water discharged from the decanter or the like even when the PTA mother liquor contains several thousands ppm in total of the aromatic carboxylic acids, and at the same time to recover, from the bottom of the tower, most of the aromatic carboxylic acids in the PTA mother liquor as the solution thereof in acetic acid.

The water discharged from the decanter or the like, which contains a small amount of the azeotrope forming agent, is subjected to a method in which the azeotrope forming agent is removed by blowing steam or gas in the water or to a method in which the water is treated with activated carbon, and thereafter the water thus treated is sent to an effluent water treatment unit.

As a method for the purpose of further reducing the effluent water treatment load, it is possible to send the water discharged from the decanter to the step b), where it is reused as a solvent for dissolving crude terephthalic acid.

By virtue of the specific constitution of the process according to the present invention it is possible to recover most part of the aromatic carboxylic acids that are contained in the PTA mother liquor by being dissolved in the acetic acid which is taken out from the distillation tower at the bottom thereof, to effectively utilize the p-toluic acid as an effective ingredient by feeding the recovered acetic acid to the oxidation step. This serves to remarkably reduce the load imposed on the effluent water treatment unit for the highly pure terephthalic acid production plant, and at the same time to markedly enhance the yield of the terephthalic acid. It is also made possible to decrease the quantity of effluent water by reusing the water which is discharged from the distillation tower as the water for the refining step of crude terephthalic acid, whereby the load put on the effluent water treatment is further curtailed to a great extent.

The process according to the present invention is characterized by its capability of recovering the useful ingredients in the PTA mother liquor without necessitating particular investment, thus rendering itself highly significant from the industrial point of view.

In the following, the present invention will be described in more detail with reference to non-limitative examples. There was used, as the PTA mother liquor for the starting material in each of the examples, the mother liquor which had been discharged from a commercial-scale plant for the production of highly pure terephthalic acid. The mother liquor was analyzed by high-performance liquid chromatography with the results shown as follows.

| Content of p-toluic acid | 882 ppm |
|---|---|
| Content of benzoic acid | 125 ppm |

EXAMPLE 1

The PTA mother liquor was incorporated with n-butyl acetate with the amount by weight the same as that thereof, and the resultant mixture was sufficiently stirred in an incubator set to 85° C. and allowed to stand. Thereafter, determinations were made of the aromatic carboxylic acids in both of the water layer and the layer of the n-butyl acetate with the results given in Table 1.

TABLE 1

| | Water layer | n-Butyl acetate layer | Partition ratio % |
|---|---|---|---|
| p-Toluic acid | 12 ppm | 801 ppm | 67 |
| Benzoic acid | 5 ppm | 115 ppm | 23 |

As can be seen from Table 1, most of the aromatic carboxylic acids in the PTA mother liquor was extracted into n-butyl acetate.

EXAMPLE 2

Acetic acid hydrate with 18% content of water was continuously fed to an intermediate stage of a distillation tower of an Oldshue fractionator system with an inside diameter of 32 mm and 42 perforated trays, where azeotropic distillation was carried out by feeding n-butyl acetate as the azeotrope forming agent to the tower at the top thereof, so that concentrated acetic acid was continuously withdrawn from the tower at the bottom thereof, and reflux liquid was fed to the top of the tower. The water distilled away through the top was condensed and continuously introduced in an extraction vessel equipped with an intensive stirring unit, to which was continuously fed the PTA mother liquor. The mixed liquid in the vessel was continuously taken out from the vessel and introduced in a decanter to separate n-butyl acetate as the upper layer liquid and again feed it to the tower at the top thereof. The water separated in the decanter as the lower layer was divided into two streams, one of which was fed as the aforesaid reflux liquid to the tower at the top thereof and the other of which was discharged. During the distillation, the reflux ratio was set to 1.0, and the temperatures in the extraction vessel and the decanter were each regulated to the range of from 85° to 90° C.

After about 6 hours of continuous azeotropic distillation, when it was confirmed that the reaction system in whole became a steady state, low-pressure steam was blown into the discharged water for a period of 15 minutes to remove residual n-butyl acetate. The resultant water was analyzed to determine the concentrations of aromatic carboxylic acids and n-butyl acetate with the results given as follows.

| p-Toluic acid | 21 ppm |
|---|---|
| Benzoid acid | 13 ppm |
| n-butyl acetate | 67 ppm |

EXAMPLE 3

The water discharged from the decanter in Example 2 was passed through an activated carbon bed at room temperature. As a result, the water thus treated contained 3 ppm of n-butyl acetate with negligible odor thereof.

EXAMPLE 4

Catalytic hydrorefining treatments were put into practice for crude terephthalic acid which has been produced on a commercial scale as the raw material, by the use of the water obtained in Example 2 and that in Example 3, and also as a reference, pure water. The analytical values of the crude terephthalic acid used as the raw material are as follows.

| $OD_{340}$ | 0.167 |
|---|---|
| 4CBA | 3480 ppm |

Crude terephthalic acid in an amount of 300 g and 900 g of water were placed in a 2 liter (L) stainless-steel made pressure-resistant vessel equipped with a stirrer, a heater, a gas introduction port and an electromagnetic catalyst cage capable of being raised and lowered from outside. The cage was packed inside with palladium/carbon catalyst in an amount of 16 g on wet basis which catalyst had been in continuous use for a period of one year in a hydrorefining treatment unit on a commerical scale. Prior to the operation, dilute aqueous ammonia was used to remove the contaminants in the catalyst, followed by sufficient washing with water.

The cage was suspended in the gaseous phase in the upside of the vessel. Hydrogen gas was introduced through a gas introduction tube into the vessel to sufficiently replace the inside of the system several times repeatedly, and subsequently was charged thereinto to a pressure of 10 kg/cm²G. Temperature raising for the content in the vessel was started under stirring and continued until it was confirmed that the temperature therein settled to 282°. Subsequently the cage was lowered to be submerged in the solution. After the lapse of 20 minutes, the cage was raised to the original place, and the content in the vessel was cooled to around room temperature to form slurry, which was filtered with a G3 glass filter. The resultant cake was washed with pure water at around 90° C. and then dried at 110° C. to afford highly pure terephthalic acid.

The results of analysis for each of the highly pure terephthalic acid thus obtained by the use of the water formed in Example 2, that in Example 3 and pure water are given in Table 2.

TABLE 2

| Water used | OD$_{340}$ | 4CBA |
|---|---|---|
| Pure water | 0.102 | 8.3 ppm |
| Water obtained in Example 2 | 0.098 | 7.9 ppm |
| Water obtained in Example 3 | 0.103 | 7.1 ppm |

No difference in the reaction was observed among the above three experiments, and the difference in the analytical results among the same in Table 2 was within the scope of reasonable errors.

The experimental results in the examples carried out in the above-mentioned manner are summarized as follows.

(1) Most of the p-toluic acid and benzoic acid contained in the PTA mother liquor are extracted into n-butyl acetate.

(2) The n-butyl acetate which has been used for the extraction of the PTA mother liquor can be employed as an azeotrope forming agent to be fed to the distillation tower without causing any trouble or disadvantage.

(3) The n-butyl acetate, which is contained in a small amount in the water formed by steam heating the water discharged from the decanter at the bottom thereof, is removed for the most part by treating with activated carbon.

(4) The water which is formed by steam heating the water discharged from the decanter at the bottom thereof, and the water which is formed by treating the aforesaid steam-treated water can each be used as a solvent for the catalytic hydrorefining treatment of the crude terephthalic acid without any problem.

What is claimed is:

1. A process for producing highly pure terephthalic acid comprising:
   (a) oxidizing a p-phenylene compound in a liquid phase in the presence of an acetic acid solvent, to produce a liquid-phase oxidation product,
   (b) separating the liquid-phase oxidation product from step (a) into the following:
       (i) a first mother liquid containing the acetic acid solvent and
       (ii) a crude terephthalic acid,
   (c) evaporating, in whole or in part, the first mother liquid from step (b), to produce a vapor,
   (d) feeding the vapor from step (c), or a condensate thereof, to an intermediate stage of a distillation tower, carrying out an azeotropic distillation in said distillation tower and withdrawing through a bottom of the distillation tower a concentrated acetic acid,
   (e) subjecting the crude terephthalic acid from step (b) to a refining treatment selected from the group consisting of a catalytic hydrotreatment, a catalytic treatment and a recrystallization, which is carried out in the presence of a solvent which is water,
   (f) cooling and crystallizing the resultant liquid from step (e), to produce a pure terephthalic acid and a second mother liquor,
   (g) subjecting the second mother liquor from step (f) to an extraction treatment in the presence of an azeotrope-forming agent to extract aromatic carboxylic acids contained in said second mother liquor, to produce a liquid extract, and
   (h) recycling the liquid extract from step (g) to the distillation tower in step (d).

2. The process according to claim 1, wherein the p-phenylene compound has a carboxyl group at a para position or a substituent selected from the group consisting of methyl, ethyl, propyl, isopropyl, formyl and acetyl.

3. The process according to claim 1, wherein the p-phenylene compound is p-xylene.

4. The process according to claim 1, wherein the liquid phase oxidation of step (a) is carried out in the presence of a catalyst selected from the group consisting of manganese, cobalt, iron, chromium and nickel.

5. The process according to claim 4, wherein the liquid phase oxidation of step (a) is carried out in the presence of an oxidation agent selected from the group consisting of molecular oxygen and air, at a temperature of 160° C. to 220° C.

6. The process according to claim 1, wherein an azeotropic mixture is withdrawn from the top of the distillation tower in step (d) and is separated into the azeotrope forming agent and water, and a part of the water thus separated is is recycled to step (e) to be used as the water solvent.

7. The process according to claim 6, wherein the azeotrope forming agent thus separated is recycled to step (g) to be used as the extracting agent.

8. The process according to claim 1, wherein the crude terephthalic acid is subjected to catalytic hydrotreatment in step (e).

9. The process according to claim 8, wherein the catalytic hydrogenation is carried out in the presence of hydrogen and a catalyst selected from the group consisting of palladium, platinum, ruthenium and rhodium, at a temperature of 260° C. to 300° C., at a hydrogen partial pressure of 50 to 100 atm, and for 2 to 20 minutes.

10. The process according to claim 1, wherein the azeotrope forming agent is n-butyl acetate.

11. The process according to claim 1, wherein the aromatic carboxylic acids extracted in step (g) are selected from the group consisting of p-toluic acid and benzoic acid.

12. The process according to claim 1, wherein the azeotrope-forming agent is selected from the group consisting of toluene, xylene, ethylbenzene, methyl butyl ketone, chlorobenzene, ethyl amyl ether, butyl formate, n-butyl acetate, isobutyl acetate, amyl acetate, n-butyl propionate and isobutyl propionate.

13. The process according to claim 12, wherein the azeotrope forming agent is in an amount of 0.1 to 2 parts by weight based on 1 part by weight of the second mother liquor.

14. The process according to claim 13, wherein the azeotrope forming agent is n-butyl acetate and the aromatic carboxylic acids extracted in step (g) comprise p-toluic acid and benzoic acid.

* * * * *